(12) United States Patent
Nilsson et al.

(10) Patent No.: US 6,582,543 B1
(45) Date of Patent: Jun. 24, 2003

(54) METHOD AND APPARATUS FOR MANUFACTURING BELTED GARMENTS

(75) Inventors: Lennart Nilsson, Skarhamn (SE); Michael Rieck, Hovas (SE); Richard Schollin, Onsala (SE); Stefan Westergard, Torslanda (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/600,755

(22) PCT Filed: Jan. 20, 1999

(86) PCT No.: PCT/SE99/00071

§ 371 (c)(1),
(2), (4) Date: Oct. 10, 2000

(87) PCT Pub. No.: WO99/37263

PCT Pub. Date: Jul. 29, 1999

(30) Foreign Application Priority Data

Jan. 21, 1998 (SE) ................................. 9800133

(51) Int. Cl.[7] .................................................. A61F 13/56
(52) U.S. Cl. ....................... 156/216; 156/226; 156/475; 156/476
(58) Field of Search ................. 156/216, 476, 156/479, 226, 227, 475, 152; 604/391, 392; 2/321

(56) References Cited

U.S. PATENT DOCUMENTS

| 3,618,608 A | * | 11/1971 | Brink ........................ 604/391 |
| 3,847,702 A | | 11/1974 | Jones, Sr. |
| 5,706,524 A | | 1/1998 | Herrin et al. |
| 5,733,275 A | | 3/1998 | Davis et al. |
| 5,795,433 A | * | 8/1998 | Niedermeyer ............... 156/479 |
| 6,342,050 B1 | * | 1/2002 | Rönnberg et al. ........... 604/392 |

FOREIGN PATENT DOCUMENTS

| DE | 37 17 042 | 12/1988 |
| FR | 2 586 558 | 3/1987 |
| WO | WO 94/26222 | 11/1994 |

* cited by examiner

Primary Examiner—Michael W. Ball
Assistant Examiner—Barbara J. Musser
(74) Attorney, Agent, or Firm—Young & Thompson

(57) ABSTRACT

A method and apparatus for manufacturing a belted garment includes: placing a first belt half and a second belt half in a partially overlapping relationship such that first end regions of the first and second belt halves contact each other in a region of overlap, and second end regions of the first and second belt halves remain uncovered; releasably joining together the first end regions to create a temporary laminate; bringing a first surface of a carrier web and the temporary laminate into mutual contact such that the first surface of the carrier web contacts the laminate in the region of overlap of the first end regions of the belt halves, and causing at least a portion of the second end region of the first belt and second belt halves to contact a second surface of the carrier web.

23 Claims, 5 Drawing Sheets

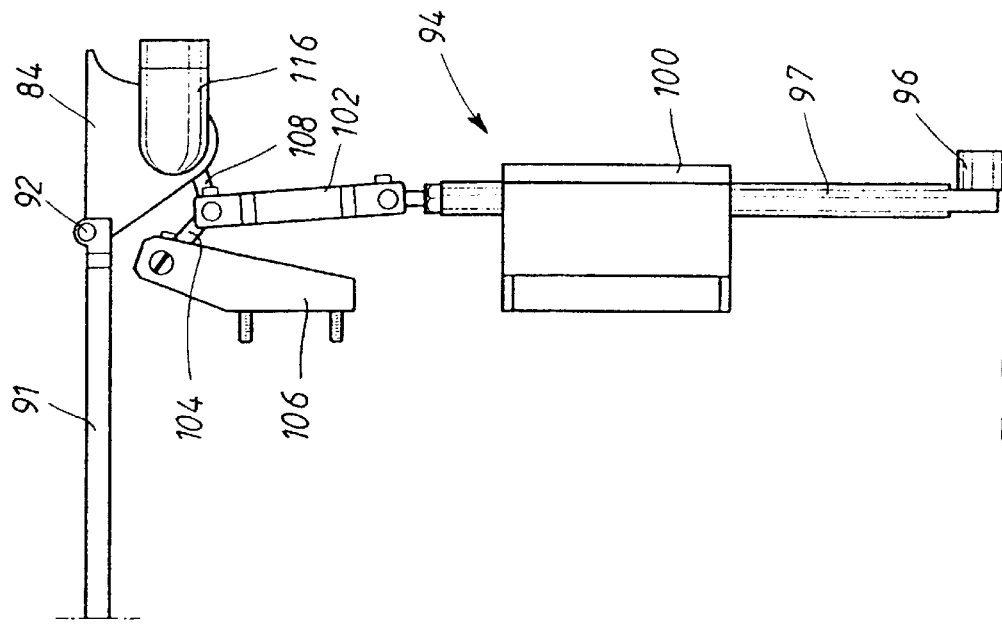
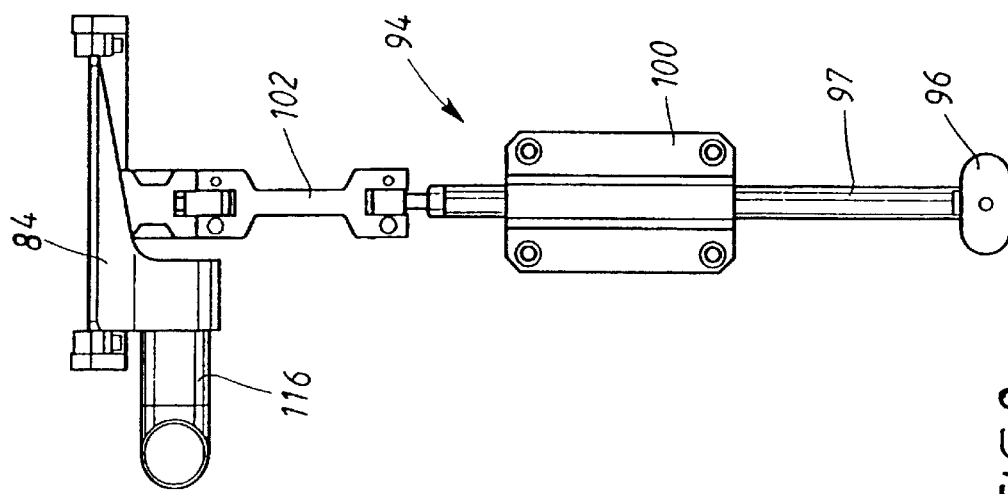

METHOD AND APPARATUS FOR MANUFACTURING BELTED GARMENTS

CROSS REFERENCE TO RELATED APPLICATION

This is the 35 USC 371 national stage of International Application PCT/SE99/00071 filed on Jan. 20, 1999 which designated the United States of America.

TECHNICAL FIELD

The present invention relates to a method and apparatus for manufacturing belted garments in which the method includes applying two belt halves to a web of carrier material.

BACKGROUND OF THE INVENTION

Garments in the form of disposable diapers are generally known in which the diaper is provided with a fastening system comprising a pair of fastening tabs secured to both sides of one end region of the diaper. The fastening tabs are intended to engage receiving means located on the other end region of the diaper. Such a diaper is generally placed on the wearer when the wearer is lying down.

Whilst the above-described fastening arrangement is satisfactory when applying diapers to a young child or baby, problems can arise when trying to fit an incontinence diaper to an adult wearer. This is particularly true for wearers who wish to apply the diaper to themselves.

It has been shown that a belted garment is easier to apply to a wearer who is standing. An example of a belted incontinence garment is described in FR-A-2 586 558 in which an absorbent chassis is provided with belt webs on both sides of a first longitudinal end. The webs are intended to be fastened around the waist of the wearer while the absorbent chassis hangs down between the legs of the wearer. Once the webs have been joined together, the wearer can then reach between his or her legs to draw up the absorbent chassis between the legs and to attach the free end of the absorbent chassis to the belt webs.

Although belted diapers may offer considerable advantages for certain groups of wearers, they are generally more difficult to manufacture than conventional diapers. This is due in part to the fact that the belt or belt halves are considerably longer than conventional fastening tabs and have to be secured to the chassis of the diaper on a rapidly moving production line. Due to the speed of the production line which is necessary for the economic viability of the product, it is imperative that the belt or belt halves do not snag or fasten in any machinery of the production line, otherwise the production would be interrupted.

SUMMARY OF THE INVENTION

It is therefore an object of the present invention to provide a method and apparatus for manufacturing belted garments, which method and apparatus permit more viable mass production of the garments.

This object is achieved in accordance with the present invention by the method and apparatus recited in the claims.

BRIEF DESCRIPTION OF THE DRAWINGS

The present invention will be described in greater detail in the following with reference to the attached drawings, in which:

FIG. 8　is a front elevation of jaw operating means incorporated in the apparatus of the present invention,
and
FIG. 9　is a side elevation of jaw operating means incorporated in the apparatus of the present invention.

DETAILED DESCRIPTION OF PREFERRED EMBODIMENTS

Figure 1:
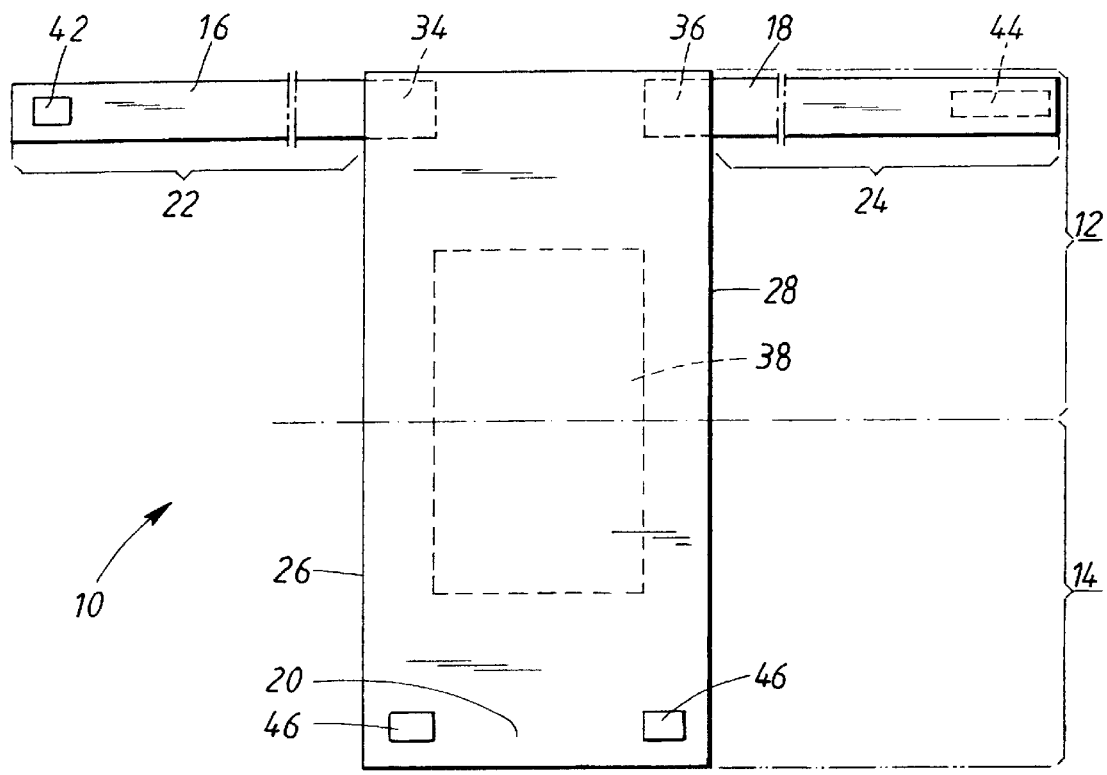
FIG. 1　is a schematic plan view of a belted garment.
Figure 2:
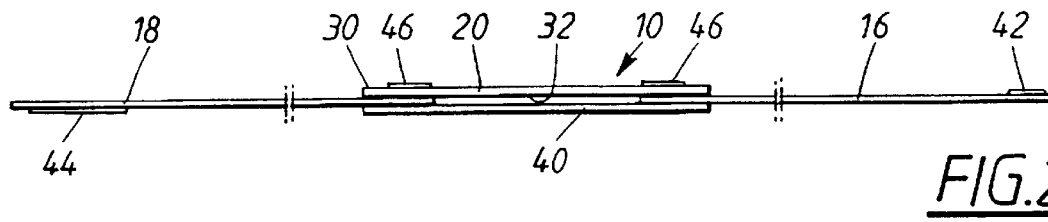
FIG. 2　is a schematic end view of the garment of FIG. 1.

In FIGS. 1 and 2, reference numeral 10 generally denotes a belted garment in the form of a disposable diaper. The garment 10 has a first end region 12 and a second end region 14. The first end region 12 is provided with a pair of belt halves in the form of a first belt half 16 and a second belt half 18. The belt halves are attached to a carrier web 20 in a manner to be described later such that a first end region 22,24 of each belt half 16,18 resp. extends outwardly beyond respective longitudinal edge portions 26,28 of the garment.

In the illustrated embodiment, the carrier web 20 forms a topsheet for the diaper and may thus be made from any suitable material which is used for this purpose. Such materials include porous foams, reticulated foams, apertured plastic films (e.g. polyolefinic film), natural fibres (e.g. wood or cotton fibres), synthetic fibres (e.g. polyester, nylon, polyethylene or polypropylene or a mixture thereof) or from a combination of natural and synthetic fibres. Depending on the absorption and flow rate characteristics which are desired for the diaper, the topsheet material may be inherently hydrophillic, inherently hydrophobic or made from inherently hydrophobic fibres which have been treated to make them at least temporarily hydrophillic. The topsheet may be woven, nonwoven, spunbonded, hydro-entangled, carded, or the like. Preferably, the topsheet is a nonwoven of polypropylene fibres.

The belt halves 16, 18 may incorporate any materials which are generally comfortable against the skin of the wearer and which possess adequate strength properties for the purpose of suspending the garment. Thus, the belt halves may be in the form of a laminate comprising a nonwoven material on the side of the belt halves which contact the user and a polypropylene film.

The topsheet 20 has a first surface 30, which is intended to face the wearer in use, and a second surface 32 to which at least a portion of second end regions 34,36 of the respective belt halves 16,18 are attached in a method according to the present invention. The second surface 32 of the topsheet 20 overlies an absorbent core 38 schematically depicted in FIG. 1 by dashed lines. The absorbent core 38 may be any means which is capable of absorbing and containing liquids and body exudates. The core may be manufactured in a wide variety of sizes and shapes, such as rectangular or hour-glass, and from a number of materials. Typical materials include creped cellulose wadding, absorbent foams, absorbent sponges, absorbent gelling materials, superabsorbent polymers, etc.

On its side facing away from the topsheet 20, the absorbent core 38 is covered by a liquid-impermeable backsheet 40. As is apparent from FIG. 2, the backsheet 40 also overlies the portions of the second end regions 34,36 which are attached to the topsheet 20. The backsheet 40 may be made from any flexible liquid-impermeable material, such as polyethylene film, and is adhered to the second surface 32 of the topsheet 20 and absorbent core 38 by any suitable adhesive to thereby form an integral garment.

In order for the belt halves 16,18 to be fastened around a wearer, the first belt half 16 is provided with a first fastener means 42 which is intended to cooperate with a complementary second fastener means 44 on the second belt half 18. The first and second fastener means 42,44 may be constituent components in a mechanical fastening system. For example, the first fastener means may be a button or stud. In such case, the second fastener means will be a button hole or clasp. Preferably, however, the mechanical fastening system is a hook-and-loop fastener system. A further possibility is that the first fastener means 42 is an adhesive patch while the second fastener means 44 is a landing zone.

As is apparent from FIG. 1, the second end region 14 of the diaper 10 is provided with closure means 46. Once the belt halves 16,18 have been fastened, the second end region 14 of the diaper 10 is made to approach the fastened belt halves and is affixed thereto by means of the closure means 46 engaging not-shown corresponding receiving means on the belt halves.

A method of manufacturing the belted garment 10 shown in FIGS. 1 and 2 in accordance with the present invention will now be described with particular reference to FIGS. 3 and 4.

Figure 4:
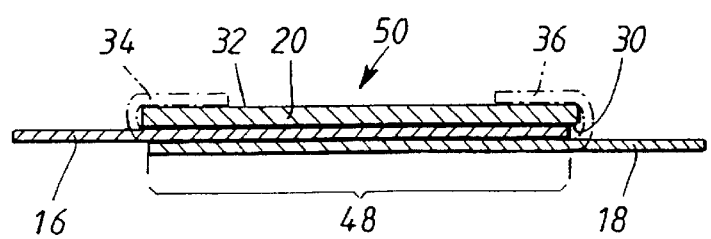
FIG. 4　is a schematic sectional view corresponding to that of FIG. 3, though showing the belted garment in a more completed state.

The method according to the present invention comprises placing the first belt half 16 and the second belt half 18 in a partially overlapping relationship such that the first end region 22 of the first belt half 16 and the first end region 24 of the second belt half 18 contact each other in a region of overlap 48 (FIG. 4). In this manner, the second end region 34 of the first belt half 16 and the second end region 36 of the second belt half 18 remain uncovered.

Figure 3:
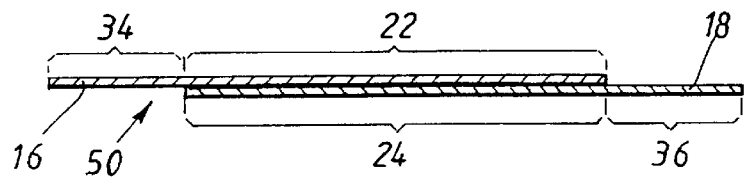
FIG. 3　is a schematic sectional view through a partially completed belted garment.

Using apparatus which will be described later, the first end regions 22,24 of the first and second belt halves 16,18 are releasably joined together, for example by applying a small amount of adhesive between the belt halves, to create a temporary laminate 50 (FIG. 3). In this respect, the expression "temporary laminate" means a laminate that a wearer is able to part without undue effort and without destroying the constituent components of the laminate. Thereafter, the first surface 30 of the carrier web 20 and the temporary laminate 50 are brought into mutual contact (FIG. 4) such that the first surface 30 of the carrier web contacts the laminate 50 in the region of overlap 48 of the first end regions 22,24 of the belt halves. Finally, at least a portion of the second end region 34 of the first belt half 16 and at least a portion of the second end region 36 of the second belt half 18 are caused to contact the second surface 32 of the carrier web, for example by bending the second end regions of the belt halves through approximately 180 degrees.

In order to maintain the portions of the second end regions 34,36 of the belt halves in contact with the second surface 32 of the carrier web 20, the second surface 32 may be coated with an adhesive.

In a preferred embodiment of the method according to the present invention, the step of bringing the first surface 30 of the carrier web 20 and the temporary laminate 50 into mutual contact comprises releasably joining the first surface of the carrier web to the temporary laminate. This may be achieved by, for example, mechanical engagement between material of the carrier web 20 and material of the temporary laminate 50 through embossing or needling.

Apparatus according to the present invention for carrying out the above-described method is shown in FIGS. 5 to 8.

Figure 5:
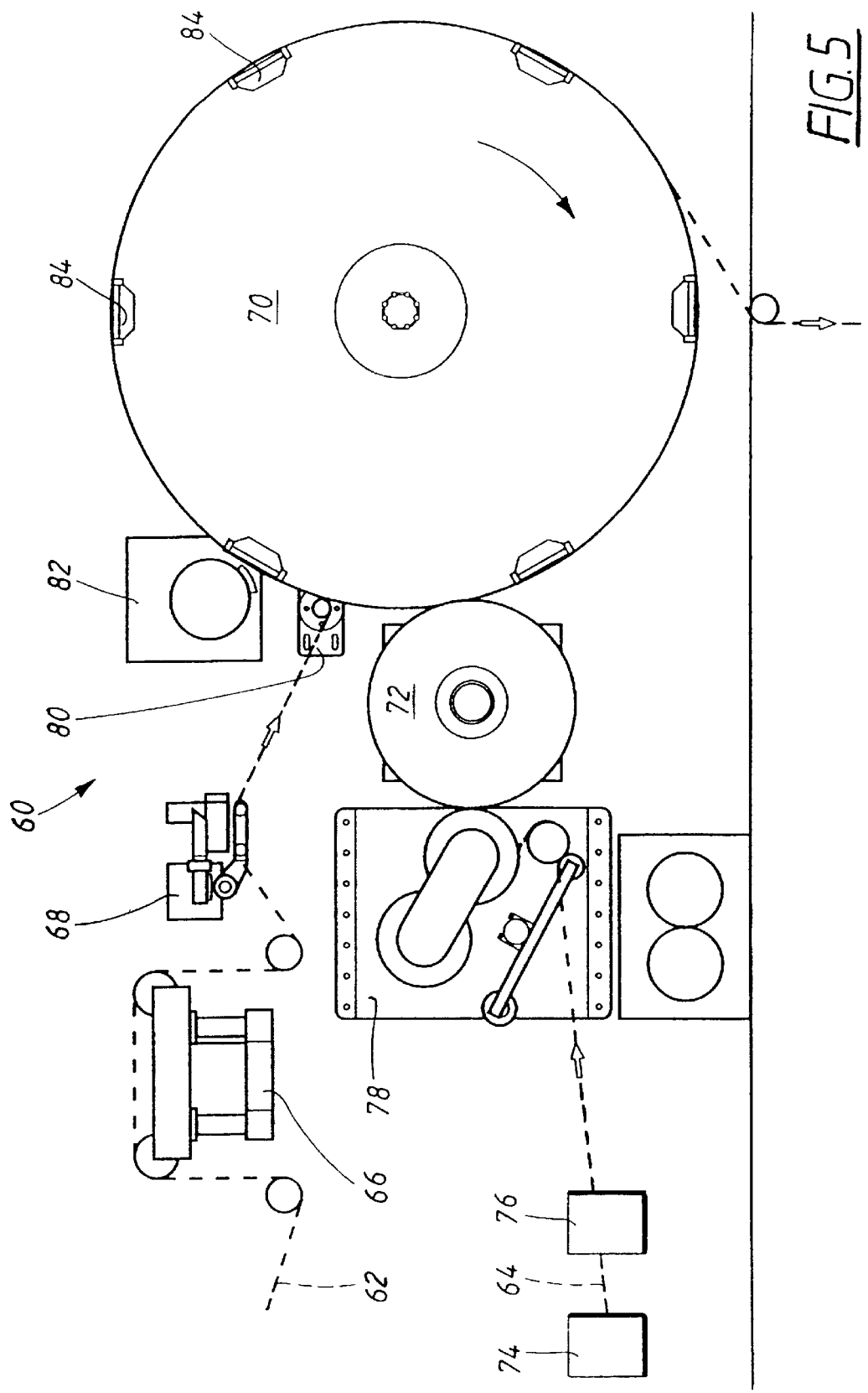
FIG. 5　is a schematic elevational view of a first embodiment of apparatus according to the present invention.
Figure 6:
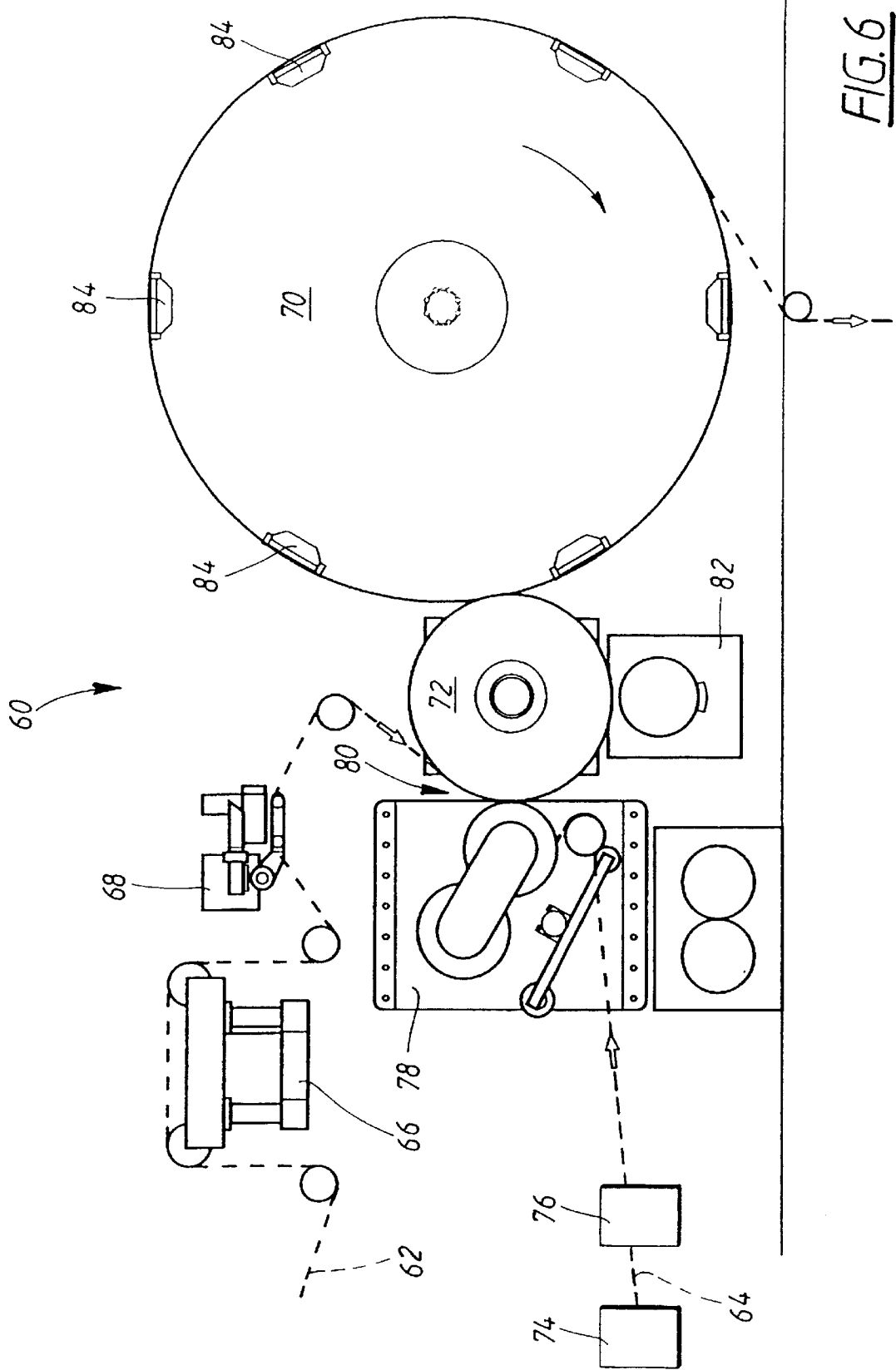
FIG. 6　is a schematic elevational view of a second embodiment of apparatus according to the present invention.

In FIGS. 5 and 6, reference numeral 60 generally denotes apparatus according to the present invention. The apparatus comprises a first web path 62 for the material forming the carrier web 20 and a second web path 64 for the material forming the belt halves 16,18. In the embodiments illustrated in FIGS. 5 and 6, the material forming the carrier web 20 is a continuous web which is fed along the first web path 62 from a not shown reel of material. The carrier web travels from the reel to an alignment station 66 which serves to ensure that the carrier web is in correct lateral alignment before passing to a gluing station 68 at which the second surface 32 of the carrier web 20 is coated with adhesive. The adhesive may be applied in a continuous coating or may be applied in discrete strips or dots. The adhesive may be applied to the carrier web by spraying, dribbling or by transfer rollers.

In the embodiment illustrated in FIG. 5, once the carrier web has left the gluing station 68 it proceeds to a rotating wheel 70 at which it is united with the belt halves 16,18 in a manner which will be described later.

In the embodiment illustrated in FIG. 6, however, the carrier web 20 is united with the belt halves 16,18 on a transfer wheel 72 upstream of the rotating wheel 70.

The second web path 64 for the belt halves 16,18 comprises means 74 for placing the first belt half 16 and the second belt half 18 in a partially overlapping relationship as shown in FIG. 3 such that the first end region 22 of the first belt half 16 and the first end region 24 of the second belt half 18 contact each other in the region of overlap 48. In this manner, the second end regions 34,36 of the belt halves remain uncovered. The belt halves are at this stage continuous webs of partially overlapping material. These webs exit the means 74 and proceed to means 76 for releasably joining together the first end regions 22,24 of the first and second belt halves to create the temporary laminate 50 shown in FIG. 3. The means 76 are preferably means for applying a small amount of adhesive between the first and second belt halves, though it is conceivable that other means such as mechanical engagement be employed.

Downstream of the means 76, the continuous webs forming the temporary laminate 50 enter a cutting station 78 at which the continuous webs are severed transversely to thereby create the temporary laminates 50 consisting of the actual belt halves which are to be applied to the carrier web 20.

In the embodiment shown in FIG. 5, the belt halves are placed on the transfer wheel 72 and are thereby transferred onto the rotating wheel 70. The rotating wheel, which will be described in greater detail later, carries the belt halves to means in the form of a meeting station 80 for bringing the first surface 30 of the carrier web 20 and the temporary laminate 50 into mutual contact such that the first surface 30 of the carrier web contacts the laminate in the region of overlap 48 of the first end regions 22,24 of the belt halves 16,18.

In the embodiment shown in FIG. 6, the means in the form of a meeting station 80 for bringing the first surface 30 of the carrier web 20 and the temporary laminate 50 into mutual contact is located upstream of the rotating wheel 70 and this step preferably takes place on the transfer wheel 72.

Immediately downstream of the meeting station 80 in both embodiments, the thus formed structure passes through means 82 for releasably joining the first surface 30 of the carrier web 20 to the temporary laminate 50. These means 82 may, for example, create mechanical engagement between material of the carrier web 20 and material of the temporary laminate 50 through embossing or needling. In the embodiment according to FIG. 6, the belt halves and carrier web are thereafter transferred to the rotating wheel 70.

In a manner which will be described in greater detail, in accordance with the present invention, the rotating wheel 70 comprises means 84 for causing at least a portion of the second end region 34 of the first belt half 22 and at least a portion of the second end region 36 of the second belt half 18 to contact the second surface 32 of the carrier web. In a preferred embodiment of the invention, and as shown in FIGS. 7, 8 and 9, these means 84 comprise a pair of jaws mounted for rotation with the rotating wheel 70.

Figure 7:
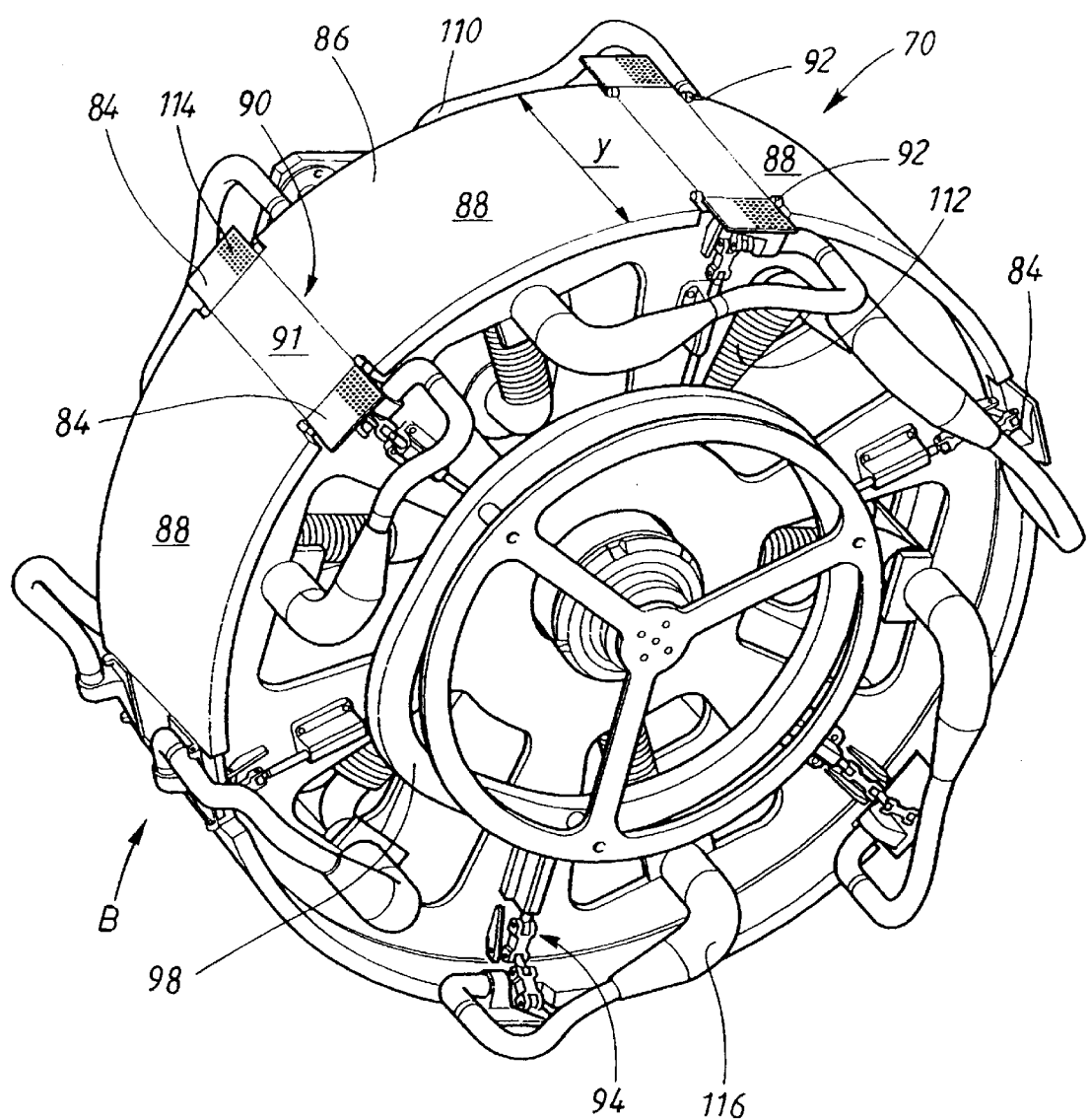
FIG. 7　is a schematic perspective view of a rotating wheel incorporated in the apparatus of the present invention.

Thus, and with particular reference to FIG. 7, the rotating wheel 70 has a peripheral surface 86 having an axial extension y. The axial extension must be equal to at least the transverse extension or width of the carrier web 20. The peripheral surface 86 is divided into a number of arcuate segments 88. Preferably, the peripheral surface in the arcuate segments 88 is coated with a material suitable for ensuring adequate friction between the rotating wheel and the carrier web 20. Such a material may suitably be a natural or synthetic rubber. The arcuate segments 88 are separated by axially extending receiving regions 90 for receiving the belt halves 16,18 from the transfer wheel 72. Each receiving region 90 comprises a pair of jaws 84 with one jaw at either axial end of an intermediate portion 91 of the receiving region. Each jaw 84 is arranged for pivotal displacement from an open position to a closed position about an axis 92 arranged substantially tangentially to the peripheral surface 86 of the rotating wheel 70. As is perhaps most clearly seen from FIG. 9, when the jaws 84 are in their open position, they form a substantially planar surface with the intermediate portion 91 of the receiving region 90 extending axially over the peripheral surface 86 of the rotating wheel.

Pivotal displacement of the jaws 84 is effected by a linkage arrangement 94 comprising a cam follower 96 located at the radially inward end of an actuation rod 97. The cam follower 96 is arranged to cooperate with a static cam surface 98 adjacent the rotating wheel 70. As is most clearly apparent from FIGS. 8 and 9, the linkage arrangement 94 includes a guide 100 affixed for rotation with the rotating wheel and adapted to guide the actuation rod 97 in the radial direction. An intermediate link 102 is pivotally attached to the radially outward end of the actuation rod 97. The intermediate link 102 is caused to follow a particular path during displacement of the actuation rod 97 due to the influence of a guide link 104 pivotally attached to both the intermediate link 102 and a static mounting 106. Displacement of the intermediate link is transferred to the jaw 84 by means of a connector rod 108.

The linkage arrangement 94 ensures displacement of the jaws 84 from an open position shown in FIGS. 8 and 9 to a closed position shown at location B in FIG. 7 and back to the open position.

With reference to FIG. 7, in order to maintain the belt halves in the receiving region 90 during rotation of the rotating wheel 70, the receiving region cooperates with two suction systems, a first suction system 110 connected to the intermediate portion 91 of the receiving region via not shown openings and a second suction system 112 connected to the jaws 84 and acting via a plurality of openings 114 on the surface which is intended to receive the belt halves. For the sake of clarity, only a few openings 114 are shown in FIG. 7, though it is to be understood that substantially the entire surface of the jaws 84 is covered with openings. Due to the fact that the jaws 84 are displaceable, the second suction system 112 includes a pivotal hose assembly 116 to permit the jaws to effect their displacement while ensuring that suction to the jaws is maintained.

To prevent the jaws 84 from snagging with the material of the belt halves 16,18 (or the carrier web should no belt halves be present), the surface of the jaws in which the openings 114 are present are advantageously coated in a low-friction material such as silicon rubber. Alternatively, this surface may be plasma treated to obtain a similar effect.

The rotating wheel 70 operates in the following manner.

In the embodiment according to FIG. 5, the transfer wheel 72 transfers the belt halves to the receiving region 90 such that the overlapping region 48 of the belt halves is received in the intermediate portion 91 of the receiving region and is held there by the first suction system. This implies that the second end regions 34,36 of the belt halves overlie the jaws 84 and are held there by the second suction system. Thereafter, the belt halves pass through the meeting station 80 at which the first surface 30 of the carrier web 20 is laid over the overlapping region 48 of the belt halves. As previously described, the thus formed structure then passes through the means 82 for releasably joining the first surface 30 of the carrier web 20 to the temporary laminate 50. Once this step has been accomplished, the jaws 84 are activated such that they pivot to their closed position, thereby folding at least a portion of the second end regions 34,36 of the belt halves 16,18 over the longitudinal edges 26,28 of the carrier web 20 to cause the portions to contact the second surface 32 of the carrier web. Obviously, the linkage arrangement 94 is designed to ensure that an adequate clamping force is attained between the portions of the second end regions 34,36 and the carrier web 20. Thereafter, the jaws 84 are opened and the carrier web with thus affixed belt halves is removed from the rotating wheel 70 for subsequent processing. The subsequent processing may include laying the absorbent core 38 over the second surface 32 of the carrier web, affixing the backsheet 40 and cutting the continuous material web of the carrier web to form individual garments.

The operation of the rotating wheel 70 in the embodiment according to FIG. 6 corresponds to that described above, though with the exception that the belt halves and carrier web are united on the transfer wheel 72 upstream of the rotating wheel.

It is to be understood that the present invention has been described above by way of example only and it will be apparent to the skilled person that the invention may be varied in many ways within the scope of the appended claims. For example, it is conceivable that suction means act over substantially the entire peripheral surface 86 of the rotating wheel 70 to thereby hold the carrier web against the rotating wheel. Furthermore, it is conceivable that the absorbent 38 and the backsheet 40 be united with the topsheet 20 on the rotating wheel 70 before the second end regions 34,36 of the belt halves 16,18 are bent over. In this manner, the second end regions 34,36 will be caused to contact the outer surface of the backsheet 40. In other words, the expression "carrier web" is to be interpreted to include a combination of topsheet and backsheet.

What is claimed is:

1. Method for manufacturing a belted garment (10), said garment comprising a first belt half (16) and a second belt half (18), each belt half having a longitudinal extension, and a carrier web (20) to which said first and second belt halves (16;18) are to be affixed, said carrier web having a first surface (30) and a second surface (32), said method comprising the steps of:

placing said first belt half (16) and said second belt half (18) in a partially overlapping relationship such that a first end region (22) of said first belt half and a first end region (24) of said second belt contact each other in a region of overlap (48), and that a second end region (34) of said first belt half and a second end region (36) of said second belt half remain uncovered;

releasably joining together said first end regions (22;24) of said first and second belt halves to create a temporary laminate (50);

bringing said first surface (30) of said carrier web (20) and said temporary laminate (50) into mutual contact such that said first surface of said carrier web contacts said laminate in said region of overlap (48) of said first end regions of said belt halves, and causing at least a portion of said second end region (34) of said first belt half (16) and at least a portion of said second end region (36) of said second belt half (18) to maintain contact with said second surface (32) of said carrier web (20).

2. The method as claimed in claim 1, wherein the step of releasably joining together said first end regions (22;24) of said first and second belt halves to create a temporary laminate (50) comprises applying adhesive between said first and second belt halves (16;18).

3. The method as claimed in claim 1, wherein the step of bringing said first surface (30) of said carrier web and said temporary laminate (50) into mutual contact comprises releasably joining the first surface (32) of the carrier web (20) to the temporary laminate.

4. The method as claimed in claim 3, wherein said releasable joining is attained by mechanical engagement between material of the carrier web and material of the temporary laminate.

5. The method as claimed in claim 4, wherein said mechanical engagement is attained by embossing.

6. The method as claimed in claim 1, wherein said portion of said second end region (34) of said first belt half (16) and said portion of said second end region (36) of said second belt half (18) are maintained in contact with said second surface (32) of said carrier web (20) by adhesive.

7. The method as claimed in claim 1, wherein the step of causing at least a portion of said second end region (34) of said first belt half (16) and at least a portion of said second end region (36) of said second belt half (18) to contact said second surface (32) of said carrier web is performed on a rotating wheel (70).

8. The method as claimed in claim 7, wherein said temporary laminate (50) is placed on said rotating wheel (70) prior to said first surface (30) of said carrier web (20) coming into contact with said temporary laminate.

9. The method as claimed in claim 7, wherein said step of bringing said first surface (30) of said carrier web (20) and said temporary laminate (50) into mutual contact takes place upstream of said rotating wheel (70).

10. The method as claimed in claim 7, wherein said temporary laminate (50) is held on said rotating wheel (70) by suction force.

11. Apparatus (60) for manufacturing a belted garment (10), said garment comprising a first belt half (16) and a second belt half (18), each belt half having a longitudinal extension, and a carrier web (20) to which said first and second belt halves are to be affixed, said carrier web having a first surface (30), a second surface (32) and a predetermined width, said apparatus comprising:

means (74) for placing said first belt half (16) and said second belt half (18) in a partially overlapping relationship such that a first end region (22) of said first belt half and a first end region (24) of said second belt half contact each other in a region of overlap (48), and that a second end region (34) of said first belt half and a second end region (36) of said second belt half remain uncovered;

means (76) for releasably joining together said first end regions (22;24) of said first and second belt halves to create a temporary laminate (50);

means (80) for bringing said first surface (30) of said carrier web (20) and said temporary laminate (50) into mutual contact such that said first surface of said carrier web contacts said laminate in said region of overlap (48) of said first end regions of said belt halves, and means (84) for causing at least a portion of said second end region (34) of said first belt half (16) and at least a portion of said second end region (36) of said second belt half (18) to maintain contact with said second surface (32) of said carrier web (20).

12. The apparatus as claimed in claim 11, wherein said means (76) for releasably joining together said first end regions (22;24) of said first and second belt halves to create a temporary laminate (50) comprises means for applying adhesive between said first and second belt halves.

13. The apparatus as claimed in claim 11, wherein said means (80) for bringing said first surface (30) of said carrier web (20) and said temporary laminate (50) into mutual contact comprises means (82) for releasably joining the first surface of the carrier web to the temporary laminate.

14. The apparatus as claimed in claim 13, wherein said means (82) for releasably joining the first surface of the carrier web to the temporary laminate comprises means for creating mechanical engagement between material of the carrier web and material of the temporary laminate.

15. The apparatus as claimed in claim 14, wherein said means (82) for creating mechanical engagement comprises an embossing station.

16. The apparatus as claimed in claim 11, wherein said means (84) for causing at least a portion of said second end region (34) of said first belt half (16) and at least a portion of said second end region (36) of said second belt half (18) to contact said second surface (32) of said carrier web (20) comprises a pair of jaws (84) pivotally mounted on a rotating wheel (70), said rotating wheel comprising a peripheral surface (86).

17. The apparatus as claimed in claim 16, further comprising a transfer wheel (72) for placing said temporary laminate (50) on said peripheral surface (86) of said rotating wheel (70) prior to said first surface (30) of said carrier web (20) coming into contact with said temporary laminate (50).

18. The apparatus as claimed in claim 16, wherein said means (80) for bringing said first surface (30) of said carrier web (20) and said temporary laminate (50) into mutual contact is located upstream of said rotating wheel (70).

19. The apparatus as claimed in claim 16, further comprising first suction means (110) cooperating with said peripheral surface (86) of said rotating wheel (70) for maintaining said temporary laminate (50) on said rotating wheel by suction force.

20. The apparatus as claimed in claim 16, wherein said peripheral surface (86) of said rotating wheel has an axial extension (y) no less than the width of said carrier web (20).

21. The apparatus as claimed in claim 16, wherein said jaws (84) are operated by cam means (98).

22. The apparatus as claimed in claim 16, wherein said jaws (84) exhibit openings (110) communicating with a second suction means (112).

23. The apparatus as claimed in claim 16, wherein said peripheral surface (86) of said rotating wheel is coated with a friction-increasing rubber material.

\* \* \* \* \*